United States Patent [19]

Larock et al.

[11] Patent Number: 4,632,996

[45] Date of Patent: Dec. 30, 1986

[54] ORGANOPALLADIUM ADDITIONS TO ALKENYL- AND METHYLENECYCLOPROPANES AND ALKENYL- AND METHYLENECYCLOBUTANES

[75] Inventors: Richard C. Larock, Ames, Iowa; Sudarsanan Varaprath, Midland, Mich.

[73] Assignee: Iowa State University Research Foundation, Inc., Ames, Iowa

[21] Appl. No.: 762,407

[22] Filed: Aug. 5, 1985

[51] Int. Cl.$^4$ ................................ C07F 15/00
[52] U.S. Cl. ............................... 549/209; 502/152; 502/156; 556/136
[58] Field of Search ............... 556/136; 549/209; 502/152, 156

[56] References Cited

U.S. PATENT DOCUMENTS

| | | | |
|---|---|---|---|
| 3,369,035 | 2/1968 | Schultz | 556/136 |
| 3,398,168 | 8/1968 | Medema | 556/136 |
| 3,584,020 | 6/1971 | Bach | 556/136 |
| 3,632,824 | 1/1972 | Fitton et al. | 556/16 |
| 3,642,902 | 2/1972 | Bach et al. | 556/136 X |
| 3,808,246 | 4/1974 | Fahey | 556/22 |
| 4,065,479 | 12/1977 | Larock | 556/136 |
| 4,101,566 | 7/1978 | Fahey | 556/22 |

Primary Examiner—Patrick P. Garvin
Attorney, Agent, or Firm—Zarley, McKee, Thomte, Voorhees & Sease

[57] ABSTRACT

(Pi-allyl)palladium compounds are prepared by organopalladium addition to alkenyl- or methylenecyclopropanes or alkenyl- or methylenecyclobutanes. The reaction is conducted in the presence of a palladium salt and involves a novel ring-opening process and a subsequent rearrangement to provide a regioselective route to (pi-allyl)palladium compounds.

9 Claims, No Drawings

ORGANOPALLADIUM ADDITIONS TO ALKENYL- AND METHYLENECYCLOPROPANES AND ALKENYL- AND METHYLENECYCLOBUTANES

GRANT REFERENCE

The invention described herein was made in part in the course of work under a grant from the National Institutes of Health No. GM 24254.

BACKGROUND OF THE INVENTION (Pi-allyl)palladium compounds have been reported in the literature and have been found useful as chemical intermediates and catalysts. For example, such compounds have gained increasing importance as catalysts for reactions of olefins and other unsaturated organic molecules, for example in processes of oligomerization.

Although the (pi-allyl)palladium compounds have been known to be used as catalysts in the types of reactions expressed herein, there has been some difficulty in obtaining these compounds in sufficiently high quantity to make them practically available for commerical organic synthesis. This is so because (pi-allyl)palladium compounds are frequently difficult to isolate from reaction mixtures and are quite often obtained in very low yields.

In a previous patent by one of the co-inventors, Larock, U.S. Pat. No. 4,065,479, issued Dec. 27, 1977, there is disclosed a process involving vinylmercurials reacting with palladium salts and simple olefins to afford (pi-allyl)palladium compounds. This invention relates to an improvement based upon the discovery that the reaction of organomercurials, palladium salts and alkenyl- or methylenecyclopropanes and alkenyl- or methylenecyclobutanes, results in a novel ring-opening process and subsequent rearrangement which affords a valuable new regioselective route to further (pi-allyl)palladium compounds.

It is accordingly a primary objective of the present invention to provide the process and synthesis route immediately discussed above to allow the practice of a novel ring-opening process and subsequent rearrangement to prepare (pi-allyl)palladium compounds from alkenyl- or methylenecyclopropanes or alkenyl- or methylenecyclobutanes.

The method of accomplishing the above objective as well as others, including the preparation and practice of the process to yield commercially practical higher yields of product, will become apparent from the detailed description which follows hereinafter.

SUMMARY OF THE INVENTION (Pi-allyl)palladium compounds are formed via organopalladium additions to alkenyl- or methylenecyclopropanes or alkenyl- or methylenecyclobutanes by reactions with an organomercurial salt selected from the group consisting of alkyl, vinyl, aryl and heterocyclic organomercurials. The reaction involves formation of a (cycloalkylcarbinyl)palladium intermediate which undergoes ring-opening and subsequent palladium migration to provide the desired (pi-allyl)palladium products in significant yields.

DETAILED DESCRIPTION OF THE INVENTION

Essentially this reaction involves a single pot reaction of an organomercurial, in the presence of a palladium salt, with an alkenyl- or methylenecyclopropane or an alkenyl- or methylenecyclobutane which, after formation of an intermediate cycloalkylcarbinyl palladium species, undergoes ring-opening and subsequent palladium migration to afford the end (pi-allyl)palladium product. The reaction may be represented by the following reaction scheme showing an organomercuric chloride as the organomercurial, reacting with an alkenylcyclobutane (n=1) or cyclopropane (n=0).

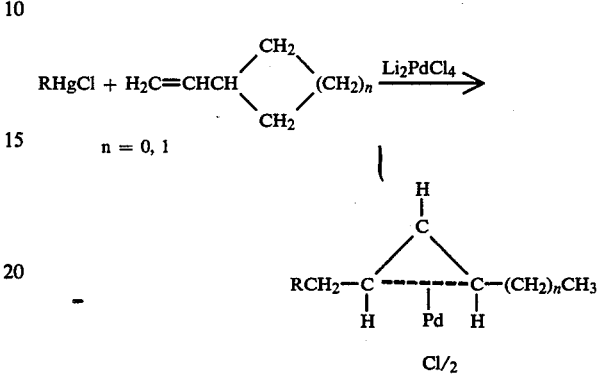

It should be understood that an organomercuric chloride is set forth as representative only. In fact, the organomercurial may be selected from those which R represents an alkyl salt, preferably $C_1$ to $C_8$, a vinylmercurial, an arylmercurial, preferably $C_6$ to $C_{18}$, but most preferably phenyl, and from heterocyclic $C_3$ to $C_8$ organomercurials. The anion of the salt is preferably a halide, preferably chloride, but may also be a nitrate, an acetate, sulfate, a phosphate, or the like, or one may use the corresponding diorganomercurials $R_2Hg$. In the reaction where R in the organomercurial is an alkyl group containing beta hydrogens, the product contains R=H.

As seen from the above starting equation, if n=0, the starting reactant is a cyclopropane derivative, and if n=1, it is, correspondingly, a cyclobutane derivative. It also should be understood that the reaction shows only the alkenyl scheme, but that a corresponding reaction occurs where the alkenyl moiety is replaced with a methylene moiety, with the only difference in product being the presence or absence of a methylene group in the (pi-allyl)palladium product.

The reaction is conducted in the presence of a palladium(II) salt. Most preferably this salt is palladium chloride, and it is preferred that the reaction is conducted in the presence of lithium chloride, in which case the reaction ingredient is often referred to as dilithium tetrachloropalladate having the formula: $Li_2PdCl_4$.

In particular, the reaction with the organomercurial is conducted in the presence of a palladium salt such as lithium trichloropalladite ($LiPdCl_3$) or dilithium tetrachloropalladate ($Li_2PdCl_4$) with the result being transmetallation by the lithium palladium salt and addition of the resulting organopalladium intermediate to the carbon-carbon double bond of the unsaturated cyclopropane or cyclobutane.

The palladium salt employed is not critical and it may be, for example, $LiPdCl_3$, $Li_2PdCl_4$, $PdCl_2$, $PdCl_2$ coordinated with acetonitrile or benzonitrile, $Pd(OAc)_2$, or $Pd(NO_3)_2$.

Pi-allylpalladium complexes are complexes in which a palladium moiety and an allylic moiety are bonded as shown below.

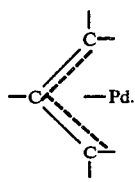

The dotted line designation represents a delocalized electron system between the three indicated carbon atoms and palladium, which delocalized system is considered to at least partially donate electrons to the palladium moiety, thereby forming the pi-allyl complex. The palladium is additionally bonded to another moiety; e.g., an anion such as chloride or bromide, and these complexes are known to exist in the form of a dimer. In terms of the class of pi-allyl palladium chloride complexes, the simplest member is pi-allyl palladium chloride which is represented by the formula:

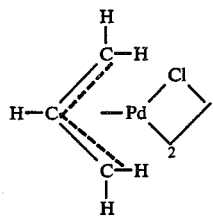

and is given the systematic name of di-μ-chloro-di-pi-allyl dipalladium. Such dimers have all of the carbon and hydrogen moieties of the compound existing in a single plane, with the palladium atom sitting above the plane of the rest of the compound, along with the halogen atom. That is to say, each pi-allyl-palladium chloride molecule, for example, is associated with a second molecule sandwiched on top of it to form a dimer.

The palladium(II) salts employed in forming the pi-allyl-palladium complexes according to the synthesis of this invention are palladium(II) salts of any of the conventional anions. They include the halides, such as chloride, bromide and iodide, sulfate, nitrate, acetate, phosphate, propionate, and others known to those skilled in the art. In summary, the precise anion of the palladium salt employed is not critical.

It is, however, preferred that the reaction be conducted in the presence of an alkali metal salt, as well as the palladium salt. The employment of an alkali metal salt in addition to the palladium salts helps in dissolving the palladium salt. Best results are obtained when the alkali metal salt is a metal halide salt such as a chloride or bromide as illustrated by sodium chloride, potassium bromide, lithium chloride, lithium bromide, and the like. Most preferably the palladium(II) salt is a palladium halide salt and a reaction equivalent amount of the salt is employed with the addition of a lithium halide salt as well. The most preferred salt is palladium chloride, and it is preferred that the reaction is conducted in the presence of lithium chloride. In this instance, the reaction ingredient is often referred to as lithium trichloropalladite or dilithium tetrachloropalladate having the formula $LiPdCl_3$ or $Li_2PdCl_4$. The added metal salt when one is employed may be added to the reaction mixture separately or alternatively added jointly with the palladium salt in the form of the coordination complex such as $LiPdCl_3$ or $Li_2PdCl\ _4$. In acetonitrile $LiPdCl_3$ is the assumed reactive salt. In most of the other solvents $Li_2PdCl_4$ is assumed to be the reactive salt.

The general procedure for conducting this reaction involves the addition of the least equivalent amounts of the organomercurial, respective cyclobutane or cyclopropane, and the palladium(II) salt. Where the olefin employed is quite volatile and quite difficult to weigh, it is preferred that two or more equivalents of the olefin are used to an equivalent amount of the organomercurial and the lithium palladium chloride salt. The reaction is preferably conducted in the presence of an organic solvent, suitable solvents being polar solvents such as tetrahydrofuran, methyl alcohol, diethyl ether, hexamethylphosphoramide, acetonitrile, and the like. Tetrahydrofuran is the preferred solvent.

The reaction is conducted under relatively mild conditions. Reaction temperatures are not critical and the reaction may be conducted at temperatures of from −20° C. up to room temperature or even higher with satisfactory results. Generally 0° C. has been found satisfactory, while allowing the reaction to proceed an appropriate period of time, in most cases within 15 minutes to 1 hour after the reaction has started. If desired, overnight reaction times may be employed. Suffice it to say that time is not a critical factor for the reaction of this invention.

Having now described the reaction of the invention in general terms, the following specific examples are offered to illustrate but not limit the process of the invention. Unless stated to the contrary in the table below, in each instance the general procedure involves the addition of two equivalents of olefin to an equivalent amount of the organomercurial and $Li_2PdCl_4$ in tetrahydrofuran at 0° C. The results of the experiments are set forth in tabular form below.

TABLE I

Examples 1-11

| example | organomercurial | olefin[a] | reaction conditions[b] | $R^1$ | $R^2$ | $R^3$ | $R^4$ | compd no.[c] | isolated yield (%) |
|---|---|---|---|---|---|---|---|---|---|
| 1 | $C_6H_5HgCl$ | 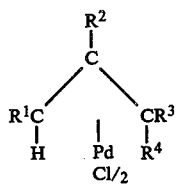 | 0° C., 2h | $CH_3$ | H | $CH_2C_6H_5$ | H | 1 | 79 |

(π-allyl)palladium compounds

TABLE I-continued

Examples 1-11

$$\underset{Cl/2}{\underset{|}{\underset{Pd}{C}}}\begin{matrix}R^2\\|\\C\\\diagup\quad\diagdown\\R^1C\qquad CR^3\\|\qquad\quad|\\H\qquad\quad R^4\end{matrix}$$

(π-allyl)palladium compounds

| example | organomercurial | olefin[a] | reaction conditions[b] | R¹ | R² | R³ | R⁴ | compd no.[c] | isolated yield (%) |
|---|---|---|---|---|---|---|---|---|---|
| 2 | CH₃HgCl | | 0° C.,2h | CH₃<br>CH₃ | H<br>H | CH₂CH₃<br>CH₃ | H<br>CH₃ | 2[d]<br>3[d] | 52 |
| 3 | C₂H₅HgCl | | 0° C.→<br>25° C.,<br>3 days | CH₃ | H | CH₃ | H | 4 | 51 |
| 4 | (CH₃)₃C\_C=C\_CH₃ / H HgCl | | 0° C.,2h | CH₃ | H | (E)—CH₂C(CH₃)=CHC(CH₃)₃ | H | 5 | 87 |
| 5 | furyl-HgCl | | 0° C.,2h | CH₃<br><br>CH₃ | H<br><br>H | CH₂-furyl<br><br>furyl | H<br><br>CH₃ | 6[e]<br><br>7[e,f] | 63 |
| 6 | C₆H₅HgCl | (methylenecyclopropane deriv.) | 0° C.,2h | CH₃<br>CH₃ | CH₃<br>CH₃ | CH₂C₆H₅<br>C₆H₅ | H<br>CH₃ | 8[g]<br>9[g] | 55 |
| 7 | | C₆H₅-cyclopropane-vinyl | 0° C.,2h | C₆H₅CH₂ | H | CH₂C₆H₅ | CH₃ | 10 | 44 |
| 8 | | C₆H₅-cyclopropane-vinyl | 0° C.,2h | C₆H₅CH₂ | H | CH₂C₆H₅ | CH₃ | 10 | 40 |
| 9 | | methylenecyclopropane | −78° C.→<br>0° C.,<br>overnight | H | C₆H₅ | CH₃ | H | 11 | 24 |
| 10 | | methylenecyclobutane deriv. | 0° C.,18h | CH₃CH₂<br>CH₃CH₂ | H<br>H | CH₂C₆H₅<br>CH₃ | CH₃<br>CH₂C₆H₅ | 12[h]<br>13[h] | 80 |
| 11 | | cyclobutene deriv. | 0° C.,18h | CH₃CH₂ | H | C₆H₅ | H | 14 | 70 |

[a] Two or more (when the olefin was quite volatile and difficult to weigh) equiv of olefin were used in all cases.
[b] All reactions were run in tetrahydrofuran.
[c] All (π-allyl)palladium compounds gave appropriate spectral data and elemental analyses.
[d] Ratio of 2 to 3 is 7:1.
[e] Ratio of 6 to 7 is 2:1.
[f] Compound 7 is a syn-anti mixture.
[g] Ratio of 8 to 9 is 5:1.
[h] Ratio of 12 to 13 is 5:1.

As can be seen in the table that aryl, methyl, ethyl, vinyl and heterocyclic organomercurials can all be employed with equally satisfactory results. Note that the use of the ethyl mercurial gives a product of palladium hydride addition (example 3). As illustrated, a variety of olefins are observed to afford (pi-allyl)palladium compounds by this procedure. Vinylcyclopropanes of various substitution patterns can be employed. Aryl substitution of the cyclopropane ring is observed to direct ring-openings toward the aryl group (examples 7 and 8). Methylene cyclopropane also undergoes this ring-opening process (example 9). One can also use alkenyl or methylene cyclobutanes with equally good results (examples 10 and 11). Generally good yields were obtained in all cases with the exception of example 9 which may have been an aberration due to the high volatility of the olefin and its high reactivity towards lithium palladium salts.

It therefore can be seen that the invention accomplishes at least all of the objectives heretofore mentioned.

What is claimed is:

1. A method of preparing (pi-allyl)palladium compounds by organopalladium addition to alkenyl- or methylenecyclopropanes or alkenyl- or methylenecyclobutanes, comprising:
   reacting an organomercurial salt selected from the group consisting of alkyl organomercurials, vinyl organomercurials, aryl organomercurials and 2-furylmercuric chloride, with an alkenyl- or methylenecyclopropane, or an alkenyl- or methylenecyclobutane, in the presence of a palladium-(II) salt to form a (cycloalkylcarbinyl)palladium intermediate which undergoes ring-opening and subsequent palladium migration to yield the desired (pi-allyl)palladium compound.

2. The method of claim 1 wherein the organomercurial is an alkyl mercury halide of $C_1$ to $C_8$ chain length.

3. The method of claim 2 wherein the alkyl group is methyl or ethyl.

4. The method of claim 1 wherein the organomercurial is a vinyl mercury halide.

5. The process of claim 1 wherein the organomercurial is an aryl mercurial.

6. The reaction of claim 5 wherein the aryl group is phenyl.

7. The method of claim 1 wherein reaction is conducted in the presence of a polar organic solvent.

8. The reaction of claim 1 wherein the reaction is conducted at a temperature of from 0° C. up to room temperature.

9. The reaction of claim 1 wherein the palladium(II) salt is dilithium tetrachloropalladate.

* * * * *